US012016937B2

(12) United States Patent
Gregoire et al.

(10) Patent No.: US 12,016,937 B2
(45) Date of Patent: Jun. 25, 2024

(54) COMPOSITION OF RADIOACTIVE AND NON-RADIOACTIVE MICROPARTICLES

(71) Applicant: ABK Biomedical Incorporated, Halifax (CA)

(72) Inventors: Marc Gregoire, Stittsville (CA); F. Anthony Headley, Jr., Greensboro, GA (US)

(73) Assignee: ABK BIOMEDICAL INCORPORATED, Halifax (CA)

( * ) Notice: Subject to any disclaimer, the term of this patent is extended or adjusted under 35 U.S.C. 154(b) by 0 days.

(21) Appl. No.: 17/295,609

(22) PCT Filed: Sep. 15, 2020

(86) PCT No.: PCT/CA2020/051240
§ 371 (c)(1),
(2) Date: May 20, 2021

(87) PCT Pub. No.: WO2021/051192
PCT Pub. Date: Mar. 25, 2021

(65) Prior Publication Data
US 2022/0211887 A1    Jul. 7, 2022

Related U.S. Application Data

(60) Provisional application No. 63/031,109, filed on May 28, 2020, provisional application No. 62/901,159, filed on Sep. 16, 2019.

(51) Int. Cl.
| *A61K 51/00* | (2006.01) |
| *A61K 9/00* | (2006.01) |
| *A61K 9/14* | (2006.01) |
| *A61K 51/12* | (2006.01) |
| *A61P 35/00* | (2006.01) |
| *G21G 1/00* | (2006.01) |
| *G21G 1/06* | (2006.01) |
| *G21G 4/08* | (2006.01) |
| *B82Y 5/00* | (2011.01) |

(52) U.S. Cl.
CPC ........ *A61K 51/1244* (2013.01); *A61K 9/0019* (2013.01); *A61K 9/141* (2013.01); *A61P 35/00* (2018.01); *G21G 1/0005* (2013.01); *G21G 1/06* (2013.01); *G21G 4/08* (2013.01); *B82Y 5/00* (2013.01)

(58) Field of Classification Search
CPC .......... A61K 9/00; A61K 51/12; A61K 51/00; A61P 35/00
See application file for complete search history.

(56) References Cited

U.S. PATENT DOCUMENTS

| 3,204,103 | A | 8/1965 | Johnson et al. |
| 4,908,019 | A | 3/1990 | Urquhart et al. |
| 5,011,677 | A | 4/1991 | Day et al. |
| 5,011,797 | A | 4/1991 | Day et al. |
| 5,302,369 | A * | 4/1994 | Day ................... A61K 51/1255 424/1.29 |
| 6,379,648 | B1 | 4/2002 | Day et al. |
| 6,537,518 | B1 * | 3/2003 | Gray .................. A61K 51/1251 424/9.1 |
| 6,916,534 | B2 | 7/2005 | Wataya et al. |
| 6,986,880 | B2 | 1/2006 | Coniglione et al. |
| 7,101,484 | B2 | 9/2006 | Betenekov et al. |
| 7,118,524 | B2 | 10/2006 | Rivard |
| 7,501,369 | B2 | 3/2009 | Tachiwana |
| 7,596,968 | B2 | 10/2009 | Marques |
| 7,659,222 | B2 | 2/2010 | Shimizu |
| 7,687,419 | B2 | 3/2010 | Kawai |
| 7,776,310 | B2 | 8/2010 | Kaplan |
| 7,842,383 | B2 | 11/2010 | Kitamura et al. |
| 7,959,900 | B2 | 6/2011 | Peng et al. |
| 7,977,264 | B2 | 7/2011 | Wolff et al. |
| 8,033,977 | B2 | 10/2011 | Hainfeld et al. |
| 8,367,575 | B2 | 2/2013 | Kuang et al. |
| 8,647,603 | B2 | 2/2014 | Aston et al. |
| 8,658,188 | B2 | 2/2014 | Stark et al. |
| 8,697,030 | B2 | 4/2014 | Peng et al. |

(Continued)

FOREIGN PATENT DOCUMENTS

| EP | 2457588 A1 | 5/2012 |
| WO | 86/03124 A1 | 6/1986 |

(Continued)

OTHER PUBLICATIONS

Hidezo Mori et al. New nonradioactive microspheres and more sensitive X-ray fluorescence to measure regional blood flow, Am J Physiol, 263, H1946-H1957. (Year: 1992).*
Etienne Garin et al. First experience of hepatic radioembolization using microspheres labelled with yttrium-90 (TheraSphere): practical aspects concerning its implementation, Eur J Nucl Med Mol Imaging, 37, 453-461. (Year: 2010).*
Amitava Mitra et al. Nanocarriers for Nuclear Imaging and Radiotherapy of Cancer, Curr Pharma Design, 12,4729-4749. (Year: 2006).*
International Application No. PCT/CA2020/051240, International Search Report and Written Opinion dated Nov. 26, 2020.
Bakker et al., "Intratumoral treatment with radioactive beta-emitting microparticles: a systematic review", Journal of Radiation Oncology, Jun. 2017, vol. 6, pp. 323-341.

(Continued)

*Primary Examiner* — Michael G. Hartley
*Assistant Examiner* — Jagadishwar R Samala
(74) *Attorney, Agent, or Firm* — Borden Ladner Gervais LLP; David Nauman

(57) ABSTRACT

The present disclosure provides a composition that includes a mixture of (i) radioactive microparticles; and (ii) non-radioactive microparticles. The radioactive microparticles may be suitable to treat a vascularized tumour, such as a liver tumour or a metastasized liver tumour. The radioactive microparticles and the non-radioactive microparticles may have substantially the same resistance when flowing in a liquid through a conduit. The present disclosure also provides methods of making and methods of using mixtures of microparticles.

29 Claims, No Drawings

(56) References Cited

U.S. PATENT DOCUMENTS

| | | |
|---|---|---|
| 8,703,097 B2 | 4/2014 | Jaffray et al. |
| 8,738,115 B2 | 5/2014 | Amberg et al. |
| 8,771,640 B2 | 7/2014 | Selwyn |
| 8,816,308 B2 | 8/2014 | Tanaka |
| 8,821,364 B2 | 9/2014 | Fisher et al. |
| 8,827,884 B2 | 9/2014 | Ribbing et al. |
| 8,837,661 B2 | 9/2014 | Wessel et al. |
| 8,865,123 B1 | 10/2014 | Day et al. |
| 8,877,662 B2 | 11/2014 | Cassingham et al. |
| 9,022,915 B2 | 5/2015 | Nakaji et al. |
| 9,119,887 B2 | 9/2015 | Day et al. |
| 9,145,331 B2 | 9/2015 | Takayama |
| 9,165,692 B2 | 10/2015 | Finger et al. |
| 9,289,625 B2 | 3/2016 | Fisher et al. |
| 9,327,038 B2 | 5/2016 | Di Pasqua et al. |
| 9,381,262 B2 | 7/2016 | Stephens et al. |
| 9,487,432 B2 | 11/2016 | Kuang |
| 9,539,347 B2 | 1/2017 | Day et al. |
| 9,597,427 B2 | 3/2017 | Keyak et al. |
| 9,623,262 B2 | 4/2017 | Vaziri et al. |
| 9,731,037 B2 | 8/2017 | Nijsen et al. |
| 9,801,962 B2 | 10/2017 | Sun et al. |
| 9,839,705 B2 | 12/2017 | Day et al. |
| 9,849,200 B2 | 12/2017 | Day et al. |
| 9,982,109 B2 | 5/2018 | Marchin |
| 10,137,149 B2 | 11/2018 | Dobson et al. |
| 10,173,920 B2 | 1/2019 | Ellison et al. |
| 2004/0136904 A1 | 7/2004 | Pitcairn |
| 2004/0197264 A1 | 10/2004 | Schwarz et al. |
| 2004/0258614 A1 | 12/2004 | Line et al. |
| 2008/0038190 A1 | 2/2008 | Simpson et al. |
| 2010/0135903 A1 | 6/2010 | Brown et al. |
| 2012/0184642 A1 | 7/2012 | Bartling et al. |
| 2014/0099255 A1 | 4/2014 | Gray |
| 2015/0273089 A1 | 10/2015 | Gray |
| 2015/0375012 A1 | 12/2015 | Herskovic |
| 2016/0008497 A1 | 1/2016 | Ricke et al. |
| 2016/0151518 A1 | 6/2016 | Stephens et al. |
| 2016/0331854 A1 | 11/2016 | Fritz |
| 2016/0367709 A1 | 12/2016 | Aston et al. |
| 2017/0007724 A1 | 1/2017 | Achilefu et al. |
| 2017/0065732 A1 | 3/2017 | Srinivas et al. |
| 2017/0129801 A1 | 5/2017 | Kikkawa et al. |
| 2017/0129802 A1 | 5/2017 | Kikkawa et al. |
| 2017/0151357 A1 | 6/2017 | Cade |
| 2017/0209606 A1 | 7/2017 | Azab et al. |
| 2018/0015154 A1 | 1/2018 | Weichert et al. |
| 2018/0057393 A1 | 3/2018 | Sakagami et al. |
| 2018/0133342 A1 | 5/2018 | Yoo et al. |
| 2018/0141853 A1 | 5/2018 | Momono |
| 2018/0222791 A1 | 8/2018 | Fotheringham et al. |
| 2018/0312425 A1 | 11/2018 | Ashton-Patton et al. |
| 2018/0354843 A1 | 12/2018 | Naito et al. |

FOREIGN PATENT DOCUMENTS

| | | |
|---|---|---|
| WO | 95/19841 A1 | 7/1995 |
| WO | 2002/034300 A1 | 5/2002 |
| WO | 2005/035005 A1 | 4/2005 |
| WO | 2016/064379 A1 | 4/2016 |
| WO | 2016055650 A1 | 4/2016 |
| WO | 2016/082045 A1 | 6/2016 |
| WO | 2017/004088 A1 | 1/2017 |
| WO | 2017/096342 A1 | 6/2017 |
| WO | 2017173440 A1 | 10/2017 |
| WO | 2017201375 A1 | 11/2017 |
| WO | 2018007643 A1 | 1/2018 |
| WO | 2018009379 A1 | 1/2018 |
| WO | 2018052741 A1 | 3/2018 |
| WO | 2018/107205 A1 | 6/2018 |
| WO | 2018200802 A1 | 11/2018 |
| WO | 2018220160 A1 | 12/2018 |
| WO | 2019009069 A1 | 1/2019 |
| WO | 2020/082168 A1 | 4/2020 |
| WO | 2020237399 A1 | 12/2020 |

OTHER PUBLICATIONS

Quirem Medical Product, "Application Note A072-me01 Microspheres for Liver Cancer Treatment", Bronkhorst USA Inc, 2018, 3 pages.

ASTM International, "Standard Practice for Characterization of Particles," West Conshohocken, PA, ASTM International, Designation: F1877-16, Oct. 2016, 15 pages.

Bult et al., "Radioactive Holmium Acetylacetonate Microspheres for Interstitial Microbrachytheraphy: An In Vitro and In Vivo stability study," Pharmaceutical Research, 2012, vol. 29, pp. 827-836.

ISO, "ISO 9276-6 Representation of Results of Particle Size Analysis—Part 6: Descriptive and Quantitative Representation of Particle Shape and Morphology", ISO Geneva, Sep. 2008, First Edition, 30 pages.

Krumbein, "Measurement and Geological Significance of Shape and Roundness of Sedimentary Particles," Journal of Sedimentary Petrology, Aug. 1941, vol. 11 (2), pp. 64-72.

Lewandowski, et al., "Sustained Safety and Efficacy of Extended-shelf-life (90)Y Glass Microspheres: Long-term Follow-up in a 134-Patient Cohort," European Journal of Nuclear Medicine and Molecular Imaging, Mar. 2014, vol. 41(3), pp. 486-493.

United States Pharmacopeia, "<776> Optical Microscopy" 2013, [online] [retrieved on Aug. 11, 2021] Retrieved from Internet:[URL: https://online.uspnf.com/uspnf/document/1_GUID-4D510FF2-03A5-443E-BE1F-5D5BFC15F5F5_1_en-US].

Westcott et al.,"The Development, Commercialization, and Clinical Context of Yttrium-90 Radiolabeled Resin and Glass Microspheres," Advances in Radiation Oncology, Oct. 2016, vol. 1(4), pp. 351-364.

Zielhuis, "Lanthanide Bearing Radioactive Particles for Cancer Therapy and Multimodality Imaging," Proefschrift Universiteit Utrecht, May 2006, pp. 1-99.

European Patent Application No. 208652438, Extended European Search Report dated Oct. 26, 2023.

Mulcahy, et al., "Radioembolization of Colorectal Hepatic Metastases Using Yttrium-90 Microspheres," Cancer, American Cancer Society, Mar. 2009, vol. 115(9), pp. 1849-1858.

Chinese Patent Application No. 202080062430, Office Action dated May 6, 2023 and English translation.

Chinese Patent Application No. 202080062430, Office Action dated Jan. 18, 2024 and English translation.

Canadian Patent Application No. 3154239, Office Action dated Feb. 27, 2024.

* cited by examiner

COMPOSITION OF RADIOACTIVE AND NON-RADIOACTIVE MICROPARTICLES

CROSS-REFERENCE TO RELATED APPLICATIONS

This application claims the benefit of U.S. Provisional Patent Application No. 62/901,159, filed Sep. 16, 2019; and of U.S. Provisional Patent Application No. 63/031,109, filed May 28, 2020. The provisional applications are incorporated by reference herein in their entirety.

FIELD

The present disclosure relates to mixtures of radioactive microparticles and non-radioactive microparticles, and uses thereof.

BACKGROUND

The following paragraphs are not an admission that anything discussed in them is prior art or part of the knowledge of persons skilled in the art.

Selective internal radiation therapy (SIRT) may be used to treat primary or metastatic hepatic malignancies. In SIRT, yttrium-90 ($^{90}Y$) radiolabeled microparticles are injected into a hepatic artery of a patient, preferentially localizing in the hepatic tumours due to their increased vascularization. The radioactive yttrium-90 labeled microparticles decay and deliver radiation to the surrounding tissue.

INTRODUCTION

The following introduction is intended to introduce the reader to this specification but not to define any invention. One or more inventions may reside in a combination or sub-combination of the apparatus elements or method steps described below or in other parts of this document. The inventors do not waive or disclaim their rights to any invention or inventions disclosed in this specification merely by not describing such other invention or inventions in the claims.

Radioactive microparticles are manufactured only in a small number of locations, and prepared for delivery to hospitals around the world. The specific activity of the microparticles are calibrated to provide a desired activity at the planned time of administration. For example, TheraSphere, a yttrium-90 glass microparticle, are prepared by neutron activation of yttrium-89 containing glass microparticles to produce microparticles having a nominal specific activity of about 110 GBq/g at the time of calibration, and are typically provided in amounts of about 1.2 million microparticles (about 3 GBq in about 27 mg) to 8 million microparticles (about 20 GBq in about 180 mg) per vial. Depending on the delay between calibration and administration, the amount of activity available to be delivered per vial may range from 0.17 GBq (1.2 million microparticles injected 9 days after calibration) to 18 GBq (8 million microparticles injected 1 day after calibration).

For a given amount of delivered radioactivity, it is believed that administering more microparticles with a lower specific activity is desirable because increasing the number of microparticles results in better tumour coverage in comparison to administering fewer microparticles at a higher specific activity. For example, in order to administer 3 GBq of radioactivity to a patient, it is believed that administering 6 million microparticles with an overall specific activity of 22 GBq/g results in better tumour coverage than administering 1.5 million microparticles at 88 GBq/g. Without wishing to be bound by theory, the authors of the present disclosure believe that microparticles come to rest with the first available localization spots in the vasculature that they encounter. Administering a smaller number of microparticles may concentrate some of the particles in one portion of the tumour if there are sufficient localization spots to interact with a significant portion of the administered particles. In contrast, administering a larger number of lower activity particles better saturates more of the available localization spots and leads to more uniform coverage in the tumour.

For at least some tumour sizes and/or degrees of vascularization, administering to the patient a mixture of (i) radioactive microparticles; and (ii) non-radioactive microparticles according to the present disclosure may provide at least some of the benefits associated with administering more microparticles at a lower specific activity, even if the individual radioactive microparticles are at a higher specific activity.

In one aspect, the present disclosure provides a therapeutic or diagnostic composition that includes a mixture of (i) radioactive microparticles; and (ii) non-radioactive microparticles.

In one aspect, the present disclosure provides a composition that includes a mixture of (i) radioactive microparticles; and (ii) non-radioactive microparticles, where the radioactive microparticles are suitable to treat a vascularized tumour, such as a liver tumour or a metastasized liver tumour, and where the radioactive microparticles and the non-radioactive microparticles have substantially the same resistance when flowing in a liquid through a conduit, such as a blood vessel.

Without wishing to be bound by theory, the authors of the present disclosure believe that microparticles that have substantially the same resistance when flowing in a liquid through a conduit will be distributed in substantially the same way throughout the tumour vasculature. Accordingly, at least for some tumour sizes and/or degrees of vascularization, mixtures of microparticles according to the present disclosure may provide improved tumour coverage over an equivalent number of radioactive microparticles administered in the absence of non-radioactive microparticles. For example, administering a mixture of (i) 1.5 million microparticles at 88 GBq/g and (ii) 4.5 million non-radioactive microparticles (that is, a total of 6 million microparticles) is expected to provide better coverage than administering only 1.5 million microparticles at 88 GBq/g, and may provide similar tumour coverage as administering 6 million microparticles at 22 GBq/g.

The radioactive microparticles may be formulated and processed to have a specific activity of 140 GBq/g to 4 GBq/g at the time of administration. In a mixture with non-radioactive microparticles, the overall specific activity of the mixture may be from about 110 GBq/g (in a mixture with 80% radioactive microparticles by mass at peak radioactivity) to about 0.4 GBq/g (in a mixture with 10% radioactive microparticles by mass once decayed to the lowest practical level of radioactivity).

The radioactive microparticles may be made from non-radioactive microparticles that are identical to the non-radioactive microparticles making up the mixture. For example, the non-radioactive microparticles in the mixture may be about 40 wt % $Y_2O_3$, about 20 wt % $Al_2O_3$, and about 40 wt % $SiO_2$, where at least some of the yttrium is yttrium-89 and none of the yttrium is yttrium-90. The radioactive microparticles in the mixture may be made from neutron activation of identical non-radioactive microparticles. The resulting radioactive microparticles would also be about 40 wt % $Y_2O_3$, about 20 wt % $Al_2O_3$, and about 40 wt % $SiO_2$, where at least some of the yttrium is yttrium-90. In such a mixture, the radioactive and non-radioactive microparticles would have essentially equal resistances when flowing in a liquid through a conduit. Such radioactive and non-radioactive microparticles would also have essentially identical densities, and essentially identical size distributions. Such radioactive and non-radioactive microparticles are expected to be equivalently distributed in the tumour.

Radioactive microparticles are not typically visible by X-ray imaging. In some examples according to the present disclosure, at least a portion of the non-radioactive microparticles in a mixture may be sufficiently radiopaque to be detectable by X-ray imaging, such as by radiography, computerized tomography (CT), cone beam CT, and/or fluoroscopy. Administering a therapeutic amount of such a mixture of microparticles may allow (i) the administration to be followed with real-time X-ray imaging, and/or (ii) for the calculation of a delivered dose of radiation to a tissue by the non-imageable radioactive microparticles based on a measured distribution of the non-radioactive, imageable particles in the tissue.

In another aspect, the present disclosure provides a method that includes exposing a first plurality of non-radioactive microparticles to neutron activation to form a plurality of radioactive microparticles; and mixing at least a portion of the plurality of radioactive microparticles with a second plurality of non-radioactive microparticles to achieve the desired overall specific activity. In particular examples, the method includes mixing the radioactive and non-radioactive particles before the level of radioactivity of the radioactive microparticles decays to 35% of the starting level of radioactivity.

In another aspect, the present disclosure provides a method for delivering radiation to a vascularlized tumour, such as a liver tumour or a metastasized liver tumour, in a patient. The method includes injecting a composition according to the present disclosure into a hepatic artery of the patient. If the non-radioactive microparticles are sufficiently radiopaque to be detectable by X-ray imaging, the method may also include imaging the administered microparticles and optionally calculating a delivered dose of radiation to a tissue by the non-imageable radioactive microparticles based on a measured distribution of the non-radioactive, imageable particles in the tissue.

Without wishing to be bound by theory, the authors of the present disclosure also believe that at least some of the benefits associated with administering a mixture of radioactive and non-radioactive microparticles can be obtained when administering radioactive and non-radioactive microparticles separately.

In one aspect, the present disclosure provides a delivery device for intravascular delivery, intra-peritoneal delivery, or percutaneous delivery of a mixture of radioactive microparticles and non-radioactive microparticles to a patient. The delivery device is fluidly coupleable to a mixing and transport medium. The delivery device includes a fluid inlet fluidly coupleable to the mixing and transport medium; a fluid outlet; a fluid mixer fluidly coupled to the fluid inlet and to the fluid outlet; a source of radioactive microparticles fluidly coupled to the fluid mixer; and a source of non-radioactive microparticles fluidly coupled to the fluid mixer. The source of the radioactive microparticles is distinct from the source of non-radioactive microparticles. The fluid mixer mixes radioactive microparticles with the non-radioactive microparticles, and delivers the mixture of radioactive and non-radioactive microparticles out of the fluid outlet utilizing the mixing and transport medium.

In another aspect, the present disclosure provides a delivery device for intravascular delivery, intra-peritoneal delivery, or percutaneous delivery of a mixture of radioactive microparticles and non-radioactive microparticles to a patient. The delivery device includes: at least one fluid inlet fluidly coupleable to a transport medium; a source of radioactive microparticles fluidly coupled to the at least one fluid inlet; a source of non-radioactive microparticles fluidly coupled to the at least one fluid inlet; a first fluid outlet fluidly coupled to the source of the radioactive microparticles; and a second fluid outlet fluidly coupled to the source of non-radioactive microparticles. The source of the radioactive microparticles is distinct from the source of non-radioactive microparticles.

In the context of the present disclosure, it should be understood that one population of microparticles is distinct from another population of microparticles if the two populations are not mixed together. For example, radioactive microparticles in the barrel of one syringe would be considered to be distinct from non-radioactive microparticles in the barrel of a second syringe even if the two syringes were fluidly coupled together and capable of expelling the microparticles together to form a mixture.

In still another aspect, the present disclosure provides a method that includes mixing (i) a first population of radioactive microparticles and (ii) a second population of non-radioactive microparticles, and administering a therapeutically or diagnostically relevant amount of the mixture to a patient.

In yet another aspect, the present disclosure provides a method of administering a therapeutically or diagnostically relevant amount of microparticles to a patient. The method includes: administering non-radioactive microparticles to the patient; and administering radioactive microparticles to the patient without first detecting the non-radioactive microparticles. The administration is by intravascular delivery, intra-peritoneal delivery, or percutaneous delivery; and the route of administration of the non-radioactive microparticles is the same as the route of administration of the radioactive microparticles.

In yet another aspect, the present disclosure provides a method of administering a therapeutically or diagnostically relevant amount of microparticles to a patient. The method includes: administering radioactive microparticles to the patient; and administering non-radioactive microparticles to the patient without first detecting the radioactive microparticles. The administration is by intravascular delivery, intra-peritoneal delivery, or percutaneous delivery; and the route of administration of the non-radioactive microparticles is the same as the route of administration of the radioactive microparticles.

In still another aspect, the present disclosure provides a method of administering a therapeutically or diagnostically relevant amount of microparticles. The method includes: concurrent administration of (i) a first population of radioactive microparticles and (ii) a second population of non-radioactive microparticles to a patient.

In still another aspect, the present disclosure provides a method of administering a therapeutically or diagnostically relevant amount of microparticles. The method includes:

sequential administration in a single treatment session of non-radioactive microparticles, and of radioactive microparticles to a patient.

In yet another aspect, the present disclosure provides a method that includes sequential administration to a patient of (i) therapeutically radioactive microparticles, and then (ii) non-radioactive microparticles.

In still another aspect, the present disclosure provides a delivery device for intravascular delivery, intra-peritoneal delivery, or percutaneous delivery of a mixture of radioactive microparticles and non-radioactive microparticles to a patient. The delivery device may be a delivery device as disclosed in WO2020/082168, which is incorporated herein by reference. A delivery device as disclosed in WO2020/082168 may be used to administer a mixture of radioactive microparticles and non-radioactive microparticles.

DETAILED DESCRIPTION

In one aspect, the present disclosure provides a mixture of (i) radioactive microparticles; and (ii) non-radioactive microparticles, where the radioactive microparticles are suitable to treat a vascularized tumour, such as a liver tumour or a metastasized liver tumour, and where the radioactive microparticles and the non-radioactive microparticles have substantially the same resistance when flowing in a liquid through a conduit. In the context of the present disclosure, a conduit may be a blood vessel or tumour vasculature.

In the context of the present disclosure, it should be understood that the radioactive microparticles and the non-radioactive microparticles in a given mixture have sufficiently the same resistance when flowing in a liquid through a conduit to behave in substantially the same way after injection into a patient.

A skilled person would understand that the resistance of an object flowing in a liquid through a conduit is reflected by the drag coefficient, and that the drag coefficient is a function of skin friction and form drag. Accordingly, resistance of a microparticle flowing in a liquid through a conduit may be affected by, for example: the size, surface area, shape, density of the microparticle, and/or surface condition of the microparticle. A skilled person would also readily understand that two different particles may have substantially the same resistance flowing in a liquid through a conduit since changing a feature to increase drag may be offset by changing another feature to decrease drag. For example, two particles may still have substantially the same drag coefficient, even though the first particle is larger than the second particle, if the surface condition of the first particle is sufficiently smoother than the surface condition of the second particle.

In the context of the current disclosure, the time it takes for a bolus of microparticles to fall a set distance through a liquid may represent the resistance of the microparticles flowing in a liquid through a conduit. This time may be measured by loading a known number of microparticles into a transparent column filled with distilled water. The number of microparticles should be selected so that the height of the bolus of microparticles is from two to five times the inner diameter of the column. Once the microparticles have settled at the bottom of the column, the column is inverted and the microparticles fall through the distilled water, with the drag counteracting the gravitational force. The total time it takes for the microparticles to fall past a transition point is measured. The transition point, measured from the top of the bolus of microparticles, is at least 100 times the inner diameter of the column. For example, in a column with an inner diameter of 0.5 cm, the settled microparticles may be 1.5 cm high, and the total fall time for the bolus of microparticles is the time it takes for all of the microparticles to fall past a point that is 50 cm away from the top of the settled microparticles.

This total fall time is compared to the total fall time for a substantially equal number of a different group of microparticles tested under the same conditions (i.e. the same fluid, the same column, the same transition point). The relative drag ratio is calculated by dividing the fall time for the first group of microparticles by the fall time for the second group of microparticles. In the context of the present disclosure, the first and the second microparticles would be considered to have substantially the same resistance when flowing in a liquid through a conduit if the relative drag ratio was from about 0.95:1 to about 1:0.95.

The radioactive microparticles and the non-radioactive microparticles in a given mixture may have substantially the same particle densities. The term "particle density" refers to the weight of an individual particle per unit volume. This is in contrast to the term "bulk density", which refers to the weight of many particles per total volume. Particle density is an intrinsic property of the material, while bulk density will change depending on the properties of the materials in the total volume.

The term "non-radioactive microparticles" should be understood to refer to microparticles whose level of radioactivity does not substantially contribute to the therapeutic or diagnostic effect of the mixture. In some examples, the non-radioactive microparticles are less than 0.15 GBq/gram, for example the non-radioactive microparticles may include Y-90 as the radioactive isotope and are less than 0.15 GBq/gram non-radioactive microparticles. In some preferable examples, the non-radioactive microparticles are 0 GBq/gram.

The particle densities of the radioactive and non-radioactive particles may be within about 30%, and preferably within about 15%, of the average. For example, the radioactive microparticles may have a particle density of 3.3 g/cm$^3$, while the non-radioactive microparticles may have a particle density of 3.9 g/cm$^3$. The difference of 0.6 g/cm$^3$ between the two types of microparticles is 16.7% of the average of the two values. Particle density may be discussed in terms of specific gravity, which is the ratio of the density of a substance to the density of a reference substance. In the context of the present disclosure, specific gravity is in reference to water.

Radioactive and non-radioactive microparticles used in compositions according to the present disclosure are selected to preferentially distribute in tumour vasculature over normal tissue. The size of the microparticles may affect this distribution. Compositions according to the present disclosure, for example that are useful for treatment of a vascularized tumour, such as a liver tumour or a metastasized liver tumour, may have average diameters from about 15 microns to about 45 microns. In particular examples, the microparticles may have average diameters from about 20 to about 35 microns.

The radioactive microparticles and the non-radioactive microparticles in a given mixture may be substantially the same size. The average sizes of the radioactive and non-radioactive microparticles may be within 40% of the average of the two average sizes. For example, the radioactive microparticles may have an average diameter of 20 microns, while the non-radioactive microparticles may have an average diameter of 30 microns. The difference of 10 microns between the two types of microparticles is 40% of the average of the two values.

An improvement in tumour coverage, for example a more uniform distribution of microparticles, may be achieved with mixtures having radioactive microparticles in an amount from about 80% to about 10% w/w of the total mass of microparticles in the composition. It should be understood that, in the context of the present disclosure, reference to any improvement is in comparison to the same number of radioactive microparticles in the absence of additional non-radioactive microparticles.

With radioactive microparticles having a high specific activity, such as 140 GBq/g, the mixtures may have fewer radioactive microparticles (such as around 10 wt %). In contrast, with radioactive microparticles having a low specific activity, such as 4 GBq/g, the mixtures may have more radioactive microparticles (such as around 80 wt %). In particular examples, such as with radioactive microparticles having a specific activity of about 88 GBq/g, the mixtures may have about 25 wt % radioactive microparticles.

It should be understood that "specific activity" refers to the radioactivity per unit mass of the radioactive microparticles, while "overall specific activity" refers to the radioactivity per unit mass of the mixture of radioactive and non-radioactive microparticles. For example, taking one gram of radioactive microparticles having a specific activity of 10 GBq/g and mixing those microparticles with one gram of non-radioactive microparticles would result in a mixture of microparticles with an overall specific activity of 5 GBq/g.

The mixture of radioactive and non-radioactive particles may be prepared in formulations at a desired radioactivity with different numbers of total microparticles. The total number of microparticles may be selected based on the tumour size and/or degree of vascularization. For example, a formulation having a radioactivity of 10 GBq in 0.5 grams of microparticles may be desirable to treat a tumour with a certain degree of vascularization, while a formulation having a radioactivity of 10 GBq in 1 gram of microparticles may be desirable to treat a more vascularized tumour. Such different formulations may be prepared by taking the same amount of radioactive microparticles and adding different amounts of non-radioactive microparticles.

Microparticles according to the present disclosure may be inorganic polymer microparticles. Inorganic polymer microparticles may be referred to herein as "glass microparticles". Radioactive glass microparticles may be formed from neutron activation of microparticles identical to the non-radioactive glass microparticles that make up the mixture. For example, a first portion of non-radioactive glass microparticles may be transformed into radioactive glass microparticles through neutron activation. These resulting radioactive glass microparticles may be mixed with a second portion of non-radioactive glass microparticles to form a composition according to the present disclosure. The first and the second portions of the non-radioactive glass microparticles may be identical, resulting in radioactive and non-radioactive microparticles having essentially identical resistances when flowing in a liquid through a conduit, essentially identical densities, and essentially identical size distributions.

Radioactive glass microparticles according to the present disclosure may include yttrium-90 as the radioactive element. Non-radioactive glass microparticles according to the present disclosure may include yttrium-89 or zirconium-90. Other radionuclei, such as radioactive isotopes of holmium, samarium, iodine, iridium, phosphorus, or rhenium, may be used in place of, or in addition to, yttrium-90.

Yttrium-89 may be transformed into yttrium-90 by exposing yttrium-89 containing microparticles to a neutron flux. The specific activity of the resulting microparticles is dependent on the level of flux and the duration of the exposure. For example, yttrium-89 may be exposed to a flux of nominally $10^{14}$ neutrons/cm$^2$/sec to effect neutron activation for a number of days to achieve a specific activity of >150 GBq/g.

Zirconium-90 may be transformed into yttrium-90 through bombarding the microparticles with a neutron beam having an energy level from about 4.7 MeV to about 12.1 MeV, as discussed in WO/2017/004088 (incorporated herein by reference).

In particular examples, the radioactive microparticles are glass microparticles having about 40 wt % $Y_2O_3$, about 20 wt % $Al_2O_3$, and about 40 wt % $SiO_2$, where at least a portion of the yttrium is yttrium-90. The radioactive microparticles may be formed by: mixing yttrium-89 oxide with ultrapure aluminum oxide and silicone dioxide; melting the mixture in a furnace at a temperature of about 1,600° C.; cooling the mixture to produce an yttrium-89 embedded glass; crushing the glass; and passing the crushed glass through a flame sprayer. The resulting spheres may be filtered through sieves to select for those with an average diameter between 20 to 40 microns. Exposure of the non-radioactive microparticles to a neutron flux may then convert at least a portion of the embedded yttrium-89 into yttrium-90.

In some examples according to the present disclosure, the radioactive microparticles are glass microparticles having about 40 wt % $Y_2O_3$, about 20 wt % $Al_2O_3$, and about 40 wt % $SiO_2$, where at least a portion of the yttrium is yttrium-90; and the non-radioactive microparticles are glass microparticles having about 40 wt % $Y_2O_3$, about 20 wt % $Al_2O_3$, and about 40 wt % $SiO_2$, where none of the yttrium is yttrium-90. The radioactive glass microparticles may be formed from a first portion of non-radioactive glass microparticles, and mixed with a second portion of non-radioactive glass microparticles. The first and the second portions of the non-radioactive glass microparticles may be identical, resulting in radioactive and non-radioactive microparticles having essentially identical resistances when flowing through a fluid, essentially identical densities, and essentially identical size distributions.

The radioactive glass microparticles and the non-radioactive glass microparticles used in compositions according to the present disclosure may have a specific gravity from about 3.3 to about 3.9 with reference to water and have an average diameter from about 20 to about 40 microns.

Alternatively, microparticles according to the present disclosure may be resin-based microparticles. Radioactive resin-based microparticles may be formed from ionic bonding of a radioactive element to particles identical to the non-radioactive resin-based microparticles. For example, radioactive resin-based microparticles may be formed through ion-exchange of a non-radioactive cation attached to the resin-based microparticles for a radioactive cation in solution in an ion-exchange process. The radioactive cation attached to the resin-based microparticles may be further immobilized on the resin through precipitation of the radioactive cation with an anion to form a low-solubility salt.

Radioactive resin-based microparticles according to the present disclosure may include yttrium-90 as the radioactive element. Yttrium-90 may be incorporated into a non-radioactive biocompatible microparticles that is coated with a partially cross-linked cation exchange polystyrene resin through ion exchange of sodium attached to the non-radioactive microparticles for yttrium-90 dissolved in the ion exchange solution. The exchanged yttrium-90 may be precipitated and immobilized on the resin-based microparticles through the precipitation of the corresponding phosphate salt, as discussed in WO/2002/034300 (incorporated herein by reference).

In some examples according to the present disclosure, the radioactive microparticles are resin-based microparticles that include yttrium-90 phosphate salt precipitated on a partially cross-linked cation exchange polystyrene resin; and the non-radioactive microparticles are resin-based microparticles coated with a partially cross-linked cation exchange polystyrene resin. The non-radioactive microparticles may include an yttrium-89 phosphate salt precipitated thereon.

The yttrium-90 may be obtained as a daughter product of the decay process of Sr-90. Chemical separation may be used to harvest the yttrium-90 from strontium-90 generators. This may be achieved by separating yttrium-890 from a solution containing radioactive strontium-90 using a process as disclosed in U.S. Pat. No. 7,101,484 (incorporated herein by reference).

The radioactive resin-based microparticles and the non-radioactive resin-based microparticles used in compositions according to the present disclosure may have, when wet: a specific gravity from about 1.0 to about 1.2, and average diameters from about 30 to about 35 microns.

Composition according to the present disclosure, such as with resin- or glass-based microparticles, may include non-radioactive microparticles that are sufficiently radiopaque to be detectable by X-ray imaging, such as by radiography, computerized tomography (CT), cone beam CT, and/or fluoroscopy. Radiopaque microparticles may have a radiopacity of greater than 6,000 Hounsfield Units (HU) at 120 kVp, such as more than 9,000 HU at 120 kVp.

Administering to a patient a therapeutic amount of such a mixture of microparticles may allow for the calculation of a delivered dose of radiation to a tissue by non-imageable radioactive microparticles, based on a measured distribution of the non-radioactive, imageable particles in the tissue.

In compositions according to the present disclosure that include glass microparticles, the non-radioactive microparticles may be glass microparticles that include $Ga_2O_3$, $SiO_2$, and SrO, and optionally $Y_2O_3$. Such microparticles are sufficiently radiopaque that they are detectable by X-ray imaging. Examples of such a microparticle are disclosed in WO/2016/082045 (incorporated herein by reference).

One particular example of such a non-radioactive microparticle is a glass microparticle with about 0.17 mol fraction of $Y_2O_3$, about 0.05 mol fraction of SrO, about 0.167 mol fraction of $Ga_2O_3$, and about 0.613 mol fraction of $SiO_2$. Such an exemplary microparticle has a particle density of about 3.93 g/cm$^3$. A radioactive glass microparticle with about 40 wt % $Y_2O_3$, about 20 wt % $Al_2O_3$, and about 40 wt % $SiO_2$ (equivalent to mol fractions of about 0.17, about 0.19, and about 0.64, respectively) where at least a portion of the yttrium is yttrium-90, has a particle density of about 3.3 g/cm$^3$. The difference in the two densities is about 17% of the average of the two densities.

In another aspect, the present disclosure provides a method that includes exposing a first plurality of non-radioactive microparticles to a neutron flux to form a plurality of radioactive microparticles; and mixing at least a portion of the plurality of radioactive microparticles with a second plurality of non-radioactive microparticles to achieve a desired overall specific activity. Particular examples of the radioactive microparticles may be formed using methods discussed above. Particular examples of the non-radioactive microparticles are discussed above.

The mixing may include combining the radioactive microparticles with the non-radioactive microparticles in a mass ratio of about 4:1 to about 1:9, resulting in a mixture having about 80 wt % to about 10 wt % of radioactive microparticles.

The method may additionally include formulating the mixture of radioactive and non-radioactive microparticles, or the portions thereof, into compositions suitable for arterial injection, such as into compositions that include sterile water, dextrose in sterile water, or saline.

In another aspect according to the present disclosure, there is provided a method for delivering radiation to a vascularized tumour, such as a liver tumour or a metastasized liver tumour, in a patient. The method includes injecting a mixture of radioactive microparticles and non-radioactive microparticles according to the present disclosure into a hepatic artery of the patient.

When injecting a mixture of glass microparticles, the method may include injecting 20 mL of a saline/microparticle mixture at a rate of about 20 mL per minute and at a pressure not to exceed 30 psi.

When the mixture of microparticles includes non-radioactive microparticles that are sufficiently radiopaque to be detectable by X-ray imaging, the method may additionally include calculating a delivered dose of radiation to a tissue by the non-imageable radioactive microparticles, based on a measured distribution of the non-radioactive, imageable particles in the tissue. Specific examples of such additional calculating steps are discussed above.

In another aspect, the present disclosure provides a therapeutic or diagnostic composition that includes a mixture of: (i) radioactive microparticles; and (ii) non-radioactive microparticles.

The radioactive microparticles may have an average density from about 1.0 g/cm$^3$ to about 4.5 g/cm$^3$, such as an average density from about 3.3 g/cm$^3$ to about 3.9 g/cm$^3$. The non-radioactive microparticles may have an average density from 1.0 g/cm$^3$ to about 4.5 g/cm$^3$, such as an average density from about 3.3 g/cm$^3$ to about 3.9 g/cm$^3$. The radioactive microparticles and the non-radioactive microparticles may have a difference in particle densities that is within 30%, and preferably within 15%, of the average of the two particle densities.

The radioactive microparticles may have an average diameter from about 10 to about 1200 microns, such as an average diameter from about 20 to about 40 microns. The non-radioactive microparticles may have an average size from about 10 to about 1200 microns, such as an average diameter from about 20 to about 40 microns. The radioactive microparticles and the non-radioactive microparticles may have a difference in average sizes that is within 40% of the average of the two averages sizes.

In some examples, the radioactive microparticles and the non-radioactive microparticles have substantially the same resistance when flowing in a liquid through a conduit.

In some examples, the radioactive microparticles make up from about 10% to about 80%, such as about 25%, of the total mass of microparticles in the composition.

The radioactive microparticles may be bioresorbable microparticles. The non-radioactive microparticles may be bioresorbable microparticles.

The radioactive microparticles may be polymer microparticles, glass microparticles, or resin microparticles. The non-radioactive microparticles may be polymer microparticles, glass microparticles, or resin microparticles.

In some examples, the radioactive microparticles are diagnostic radioactive microparticles. In some examples, the radioactive microparticles are therapeutic radioactive microparticles.

Diagnostic radioactive microparticles may include one or more radioisotopes selected from the group consisting of: copper-67, holmium-166, indium-111, iodine-131, lutetium-177, molybdenum-99, phosphorus-32, rubidium-82, technicium-99m, and thallium-201.

Therapeutic radioactive microparticles may include one or more radioisotopes selected from the group consisting of: actinium-225, bismuth-213, copper-67, indium-111, iodine-131, iodine-125, gadolinium-157, holmium-166, lead-212, lutetium-177, palladium-103, phosphorus-32, radium-223, rhenium-186, rhenium-188, samarium-153, strontium-89, and tungsten-188.

In some examples, the non-radioactive microparticles are sufficiently radiopaque to be detectable by X-ray imaging, such as by radiography, computerized tomography (CT), cone beam CT, and/or fluoroscopy, for example having a radiopacity of greater than 6,000 Hounsfield Units (HU) at 120 kVp, such as more than 9,000 HU at 120 kVp.

In some examples, the non-radioactive microparticles include a therapeutically active compound, and the therapeutically active compound elutes from the microparticles under physiologically relevant conditions.

In some examples, the radioactive microparticles and the non-radioactive microparticles are inorganic polymer microparticles. The radioactive microparticles may be microparticles formed from neutron activation of particles identical to the non-radioactive microparticles.

The inorganic polymer microparticles may have a specific gravity from about 3.3 to about 3.9 with reference to water, and have an average diameter from about 20 to about 40 microns.

The radioactive microparticles may include yttrium-90. The non-radioactive microparticles may include yttrium-89. The non-radioactive microparticles may include zirconium-90. The non-radioactive microparticles may be sufficiently radiopaque to be detectable by X-ray imaging, such as by radiography, computerized tomography (CT), cone beam CT, and/or fluoroscopy, for example having a radiopacity of greater than 6,000 Hounsfield Units (HU) at 120 kVp, such as more than 9,000 HU at 120 kVp.

The non-radioactive microparticles may include $Ga_2O_3$, $SiO_2$, SrO, and optionally $Y_2O_3$.

The radioactive microparticles may include about 40 wt % $Y_2O_3$, about 20 wt % $Al_2O_3$, and about 40 wt % $SiO_2$, wherein at least a portion of the yttrium is yttrium-90.

In one example, the radioactive microparticles include about 40 wt % $Y_2O_3$, about 20 wt % $Al_2O_3$, and about 40 wt % $SiO_2$, where at least a portion of the yttrium is yttrium-90; and the non-radioactive microparticles include about 40 wt % $Y_2O_3$, about 20 wt % $Al_2O_3$, and about 40 wt % $SiO_2$, wherein none of the yttrium is yttrium-90.

In some examples, the radioactive microparticles and the non-radioactive microparticles are resin-based microparticles. The radioactive microparticles may be microparticles formed from ionic bonding of a radioactive element to particles identical to the non-radioactive microparticles. The radioactive element may be yttrium-90.

The non-radioactive microparticles may be are sufficiently radiopaque to be detectable by X-ray imaging, such as by radiography, computerized tomography (CT), cone beam CT, and/or fluoroscopy, for example having a radiopacity of greater than 6,000 Hounsfield Units (HU) at 120 kVp, such as more than 9,000 HU at 120 kVp.

The resin-based microparticles may have, when wet: a specific gravity from about 1.0 to about 1.2 with reference to water, and average diameters from about 30 to about 35 microns.

In another aspect, the present disclosure provides a method that includes administering a mixture of radioactive microparticles and non-radioactive microparticles, as described above, where the administration is: by intravascular delivery, intra-peritoneal delivery, or percutaneous delivery.

In a further aspect, the present disclosure provides a delivery device for intravascular delivery, intra-peritoneal delivery, or percutaneous delivery of a mixture of radioactive microparticles and non-radioactive microparticles to a patient. The delivery device is fluidly coupleable to a mixing and transport medium, and includes: a fluid inlet fluidly coupleable to the mixing and transport medium; a fluid outlet; a fluid mixer fluidly coupled to the fluid inlet and to the fluid outlet; a source of radioactive microparticles fluidly coupled to the fluid mixer; and a source of non-radioactive microparticles fluidly coupled to the fluid mixer. The source of the radioactive microparticles is distinct from the source of non-radioactive microparticles. The fluid mixer mixes radioactive microparticles with the non-radioactive microparticles, and delivers the mixture of radioactive and non-radioactive microparticles out of the fluid outlet utilizing the mixing and transport medium.

In still another aspect, the present disclosure provides a delivery device for intravascular delivery, intra-peritoneal delivery, or percutaneous delivery of a mixture of radioactive microparticles and non-radioactive microparticles to a patient. The delivery device includes: at least one fluid inlet fluidly coupleable to a transport medium; a source of radioactive microparticles fluidly coupled to the at least one fluid inlet; a source of non-radioactive microparticles fluidly coupled to the at least one fluid inlet; a first fluid outlet fluidly coupled to the source of the radioactive microparticles; and a second fluid outlet fluidly coupled to the source of non-radioactive microparticles. The source of the radioactive microparticles is distinct from the source of non-radioactive microparticles. In some examples, the delivery device delivers the radioactive microparticles and the non-radioactive microparticles in a single treatment session. In some examples, the first fluid outlet and the second fluid outlet are proximate to each other. In the context of the present disclosure, it should be understood that the fluid outlets are proximate to each other if the patient could be administered the radioactive microparticles and the non-radioactive microparticles at substantially the same time, for example over the course of a single treatment session.

The radioactive microparticles and/or the non-radioactive microparticles in the delivery devices may be as disclosed above. In some examples, the radioactive microparticles make up from about 10% to about 80%, such as about 25%, of the total mass of microparticles in the delivery device. In some examples the radioactive microparticles and the non-radioactive microparticles have substantially the same resistance when flowing in a liquid through a conduit.

In a still further aspect, the present disclosure provides a method that includes mixing (i) a first population of radioactive microparticles and (ii) a second population of non-radioactive microparticles, and administering a therapeutically or diagnostically relevant amount of the mixture to a patient. The radioactive microparticles and/or the non-radioactive microparticles in the method may be as disclosed above. In some examples, the radioactive microparticles make up from about 10% to about 80%, such as about 25%, of the total mass of microparticles used in the method. The administration may be by intravascular delivery, intra-peritoneal delivery, or percutaneous delivery.

In other aspects, the present disclosure provides a method of administering a therapeutically or diagnostically relevant amount of microparticles to a patient. The method includes either: administering non-radioactive microparticles to the patient, and administering radioactive microparticles to the patient without first detecting the non-radioactive microparticles; or administering radioactive microparticles to the patient, and administering non-radioactive microparticles to the patient without first detecting the radioactive microparticles. The administration is by intravascular delivery, intra-peritoneal delivery, or percutaneous delivery. The route of administration of the non-radioactive microparticles is the same as the route of administration of the radioactive microparticles.

In some examples, the method includes concurrent administration of the non-radioactive and the radioactive microparticles. In other examples, the method includes sequential administration of the non-radioactive and the radioactive microparticles; or sequential administration of the radioactive and the non-radioactive microparticles.

In still another aspect, the present disclosure provides a method of administering a therapeutically or diagnostically relevant amount of microparticles. The method includes: concurrent administration of (i) a first population of radioactive microparticles and (ii) a second population of non-radioactive microparticles to a patient.

In some examples, the first population of radioactive microparticles is distinct from the second population of non-radioactive microparticles. The first population of radioactive microparticles and the second population of non-radioactive microparticles may be administered as a mixture.

In yet another aspect, the present disclosure provides a method of administering a therapeutically or diagnostically relevant amount of microparticles. The method includes sequential administration in a single treatment session of non-radioactive microparticles, and of radioactive microparticles to a patient.

In still another aspect, the present disclosure provides a method that includes sequential administration to a patient of (i) therapeutically radioactive microparticles, and then (ii) non-radioactive microparticles.

In some examples, sequential administration includes intermittent administration of the non-radioactive microparticles and the radioactive microparticles. The intermittent administration may include alternating administration of the non-radioactive microparticles and the radioactive microparticles.

In some examples, sequential administration includes administration of all of one type of microparticles before administration of the next type of microparticles. For example, sequential administration may include administration of all of the non-radioactive microparticles before administration of any of the radioactive microparticles; or administration of all of the radioactive microparticles before administration of any of the non-radioactive microparticles.

Methods according to the present disclosure may deliver a therapeutically relevant amount of radiation to the patient, or may deliver a diagnostically relevant amount of non-radioactive microparticles to the patient.

In some examples of the above-described methods, the radioactive microparticles includes a diagnostically detectable radioisotope; the non-radioactive microparticles include a therapeutically active compound that elutes from the microparticles under physiologically relevant conditions; and the method delivers a diagnostically relevant amount of the radioactive microparticles to the patient and a therapeutically relevant amount of the non-radioactive microparticles to the patient.

In methods according to the present disclosure: the administration may be by intravascular delivery, intra-peritoneal delivery, or percutaneous delivery; the radioactive microparticles and/or the non-radioactive microparticles may be as discussed above; about 10% to about 80%, such as about 25%, of the total mass of microparticles delivered may be radioactive microparticles; or any combination thereof.

In various examples of the compositions, the delivery devices, and the methods disclosed herein, the radioactive microparticles and the non-radioactive microparticles may have substantially the same resistance when flowing in a liquid through a conduit; and/or the radioactive microparticles and the non-radioactive microparticles may be suitable for administration to a vascularized tumour, such as a liver tumour or a metastasized liver tumour.

Although the above discussion relates to methods of administering radioactive microparticles and non-radioactive microparticles, the present disclosure equally contemplates the corresponding "uses" of the microparticles, including microparticles useful in the disclosed methods, and uses of microparticles in the manufacture of an administrable formulation useful in the disclosed methods.

Bulk microsphere CT radiopacity can be assessed through quantitative radiopacity measurements, expressed as Hounsfield Unit Values (HU) obtained from five replicate regions of interest (ROls, n=5) recorded from respective Axial CT scans (1 mm slice thickness, pitch=0.5, 70 kVp and 120 kVp) through 1.2 mL glass v-vials (Product Code: Z115061, Sigma Aldrich, Canada) with 500 mg microspheres in 6 μL of sterile saline. All measurements should be performed on the experimental materials within mean (±SD) diameter of 20 μm to 30 μm, using a Siemens Somatom Definition AS+ scanner (Siemens Healthcare, Erlangen, Germany) and the extended HU range option employed for scanning.

Experimental

As discussed in greater detail below, an exemplary mixture according to the present disclosure was loaded into a delivery device and subsequently transferred out of a micro-catheter, mimicking an administration to a patient. Aliquots of the mixture dispensed from the micro-catheter were collected over time and the specific activity of each aliquot was measured. The measured specific activity remained substantially constant for the aliquots that included the particles. This suggests that the hot and cold particles of the exemplary mixture did not separate during the administration from the delivery device.

Materials and Methods

Non-radioactive glass microparticles and radioactive glass microparticles were dispensed gravimetrically into a 3 mL glass vial containing water to result in 3:1 ratio by mass of non-radioactive to radioactive microparticles.

The non-radioactive microparticles had a size distribution ranging from 20-32 μm in diameter with D5<22.2 μm, D50<28.1 μm, and D90<32.8 μm, as measured with a Horiba Instruments Camsizer X2 particle size analyzer with an X-Flow module, a density of 3.36 g/cm$^3$, as measured by an AccuPyc II 1340 pycnometer, and an average sphericity of 0.985, as measured with a Horiba Instruments Camsizer X2 particle size analyzer with an X-Flow module. The radioactive microparticles included Y-90, and had a size distribution ranging from 20-32 μm in diameter with D5<20.3, D50<26.6 and D90<31.4, a density of 3.39 g/cm$^3$, and an average sphericity of 0.914.

The vials were secured with a septum held in place with a crimped seal. After the vial was vortexed for approximately 30 seconds to ensure a homogenous mixture, the radioactivity of the blended vial was measured. The measured radioactivity and mass was used to calculate the specific activity of the "unit dose".

The mixture of microparticles was loaded into a delivery device according to FIG. 9 as disclosed in WO2020/082168, which is incorporated herein by reference. The delivery device was first primed with water to remove all air in the system. The blended vial was connected to the device and drawn into the elongate housing (910) and allowed to settle into an administration position. The elongate housing (910) used in the present experiments was 21.6 cm in length, had an inner diameter of 0.078" (about 1.98 mm) and had an outer diameter of 0.125" (about 3.18 mm). This settling provided a first opportunity for the microparticles to stratify.

The settled microspheres were dispensed from the delivery device as discussed in WO2020/082168. Briefly, water was used as both the transport medium (904) and the displacement medium (906). A water-filled syringe was used to push the microspheres from the elongate housing into a fluid path that carried the microparticles out of the fluid outlet (908). The length of the tubing that made up the fluid path between the mixer (902), where the microparticles were mixed with the transport medium (904), and the fluid outlet (908) was 150 cm. The inner diameter of the tubing that made up the fluid path was 0.021" (about 0.53 mm). The travel down the fluid path provided another opportunity for the radioactive microparticles to separate from the non-radioactive microparticles.

Aliquots from the fluid outlet were collected. After collection, the radioactivity of the different aliquots were measured in a Capintec Model CRC-15R ionization chamber. After the radioactivity was measured, the water was evaporated using a hot plate so that the dry mass of the microparticles could be measured. The specific activity (radioactivity per unit mass) from each aliquot was measured and compared against the theoretical specific activity of the originally blended mixture (i.e. the unit dose).

The above procedure was performed with 100 mg and 800 mg unit doses. The results are shown in Tables 1 to 5, below. The results illustrate that the radioactive and non-radioactive microparticles in the exemplary mixture do not appreciably separate during loading of, and subsequent administration from, the delivery device.

TABLE 1

| | Dry Mass (mg) | Radioactivity (GBq) (normalized) | Calculated Specific Activity* (GBq/mg) | % Difference |
|---|---|---|---|---|
| Unit Dose Aliquot | 100.9 | 2.04 | 0.020 Sample SA | |
| 1 | 0.2 | n/a | n/a | n/a |
| 2 | 0.1 | n/a | n/a | n/a |
| 3 | 3.5 | 0.06 | 0.0166 | n/a |
| 4 | 30.3 | 0.58 | 0.0193 | 5% |
| 5 | 15.0 | 0.28 | 0.0185 | 8% |
| 6 | 7.8 | 0.14 | 0.0183 | 9% |
| 7 | 34.9 | 0.72 | 0.0206 | -2% |
| 8 | 7.0 | 0.14 | 0.0204 | -1% |

TABLE 1-continued

| | Dry Mass (mg) | Radioactivity (GBq) (normalized) | Calculated Specific Activity* (GBq/mg) | % Difference |
|---|---|---|---|---|
| 9 | 0.3 | 0.00 | n/a | n/a |
| 10 | 0.3 | 0.00 | n/a | n/a |

*with geometry factor applied

TABLE 2

100 mg unit dose

| | Dry Mass (mg) | Radioactivity (GBq) (normalized) | Calculated Specific Activity* (GBq/mg) | % Difference |
|---|---|---|---|---|
| Unit Dose Aliquot | 100.3 | 1.88 | 0.019 Sample SA | |
| 1 | 0.4 | n/a | 0.0 | n/a |
| 2 | 0.3 | n/a | 0.0 | n/a |
| 3 | 0.4 | 0.00 | 0.003 | n/a |
| 4 | 23.2 | 0.45 | 0.019 | 0% |
| 5 | 24.0 | 0.47 | 0.019 | -1% |
| 6 | 26.2 | 0.51 | 0.019 | 0% |
| 7 | 13.1 | 0.24 | 0.018 | 5% |
| 8 | 10.6 | 0.20 | 0.018 | 4% |
| 9 | 0.6 | 0.00 | 0.005 | n/a |
| 10 | 0.3 | 4.86 | 0.0 | n/a |

*with geometry factor applied

TABLE 3

800 mg unit dose

| | Dry Mass (mg) | Radioactivity (GBq) (normalized) | Calculated Specific Activity* (GBq/mg) | % Difference |
|---|---|---|---|---|
| Unit Dose Aliquot | 801.4 | 3.03 | 114.4 Sample SA | |
| 1 | 6.3 | 0.02 | 64.8 | 43% |
| 2 | 107.2 | 0.39 | 97.1 | 15% |
| 3 | 123.2 | 0.53 | 115.2 | -1% |
| 4 | 131.4 | 0.56 | 115.8 | -1% |
| 5 | 133.7 | 0.56 | 113.9 | 0% |
| 6 | 133.1 | 0.55 | 112.2 | 2% |
| 7 | 70.7 | 0.30 | 115.8 | -1% |
| 8 | 26.1 | 0.11 | 117.6 | -3% |
| 9 | 0 | 0.00 | n/a | n/a |
| 10 | 45.1 | 0.18 | 107.7 | 6% |
| 11 | 1.7 | 0.00 | 0.0 | n/a |
| 12 | 1.8 | 0.00 | 0.0 | n/a |

*with geometry factor applied

TABLE 4

800 mg unit dose

| | Dry Mass (mg) | Radioactivity (GBq) (normalized) | Calculated Specific Activity* (GBq/mg) | % Difference |
|---|---|---|---|---|
| Unit Dose Aliquot | 789.1 | 11.46 | 0.015 Sample SA | |
| 1 | 0.2 | 0.0 | n/a | n/a |
| 2 | 52.8 | 0.8 | 0.0148 | -2% |
| 3 | 95.8 | 1.42 | 0.0148 | -2% |

TABLE 4-continued 800 mg unit dose

|   | Dry Mass (mg) | Radioactivity (GBq) (normalized) | Calculated Specific Activity* (GBq/mg) | % Difference |
|---|---|---|---|---|
| 4 | 109.7 | 1.62 | 0.0147 | −2% |
| 5 | 189.4 | 2.77 | 0.0146 | −1% |
| 6 | 88.5 | 1.32 | 0.0149 | −3% |
| 7 | 97.8 | 1.46 | 0.0149 | −3% |
| 8 | 73.6 | 1.09 | 0.0148 | −2% |
| 9 | 74.9 | 1.11 | 0.0149 | −2% |
| 10 | 4.1 | 0.0 | n/a | n/a |
| 11 | n/a | 0.0 | n/a | n/a |
| 12 | n/a | 0.0 | n/a | n/a |

*with geometry factor applied

TABLE 5

800 mg unit dose

|   | Dry Mass (mg) | Radioactivity (GBq) (normalized) | Calculated Specific Activity* (GBq/mg) | % Difference |
|---|---|---|---|---|
| Unit Dose Aliquot | 790.5 | 8.81 | 0.011 Sample SA | |
| 1 | 0.0 | n/a | n/a | n/a |
| 2 | 52.9 | 0.6 | 0.0116 | −4% |
| 3 | 114.2 | 1.30 | 0.0114 | −2% |
| 4** | 77.9 | 1.30 | 0.0167 | −50% |
| 5 | 134.7 | 1.53 | 0.0114 | −2% |
| 6 | 144.9 | 1.63 | 0.0113 | −1% |
| 7 | 87.7 | 1.01 | 0.0115 | −3% |
| 8 | 42.0 | 0.49 | 0.0116 | −4% |
| 9 | 82.5 | 0.95 | 0.0115 | −3% |
| 10 | 0.0 | n/a | n/a | n/a |
| 11 | 0 | n/a | n/a | n/a |
| 12 | 0 | n/a | n/a | n/a |

*with geometry factor applied
**outlier discounted due to experimental error

In the preceding description, for purposes of explanation, numerous details are set forth in order to provide a thorough understanding of the examples. However, it will be apparent to one skilled in the art that these specific details are not required. Accordingly, what has been described is merely illustrative of the application of the described examples and numerous modifications and variations are possible in light of the above teachings.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

What is claimed is:

1. A composition comprising a mixture of:
   (i) radioactive microparticles; and
   (ii) non-radioactive microparticles,
   wherein the radioactive microparticles are suitable to treat a vascularized tumour,
   wherein the non-radioactive microparticles have a radiopacity of greater than 6,000 Hounsfield Units (HU) at 120 kVp, and have a level of radioactivity that is less than 0.15 GBq/gram,
   wherein the radioactive microparticles comprise about 40 wt % $Y_2O_3$, about 20 wt % $Al_2O_3$, and about 40 wt % $SiO_2$, wherein at least a portion of the yttrium is yttrium-90,
   wherein the radioactive microparticles make up from about 10% to about 80% of the total mass of microparticles in the composition,
   wherein the mixture of the radioactive microparticles and the non-radioactive microparticles has an overall specific activity that is 0.4 GBq/g or greater; and
   wherein the radioactive microparticles and the non-radioactive microparticles have sizes, surface areas, shapes, and particle densities that result in a relative drag ratio from about 0.95:1 to about 1:0.95, wherein the relative drag ratio is calculated by dividing the fall time for the radioactive microparticles by the fall time for the non-radioactive microparticles.

2. The composition according to claim 1, wherein the radioactive microparticles and the non-radioactive microparticles have sizes, surface areas, shapes, particle densities, and surface conditions that result in particles with a relative drag ratio of about 1.0.

3. The composition according to claim 2, wherein the radioactive microparticles and the non-radioactive microparticles have substantially the same: sizes, surface areas, shapes, particle densities, and surface conditions.

4. The composition according to claim 1, wherein the difference in particle densities of the radioactive and non-radioactive microparticles is within 30% of the average of the two particle densities.

5. The composition according to claim 1, wherein the difference in average sizes of the radioactive and non-radioactive microparticles is within 40% of the average of the two averages sizes.

6. The composition according to claim 1, wherein the radioactive microparticles make up about 25% of the total mass of microparticles in the composition.

7. The composition according to claim 1, wherein the radioactive microparticles and the non-radioactive microparticles have a specific gravity from about 3.3 to about 3.9 with reference to water, and have an average diameter from about 20 to about 40 microns.

8. The composition according to claim 1, wherein non-radioactive microparticles comprise yttrium-89.

9. The composition according to claim 1, wherein the non-radioactive microparticles comprise $Ga_2O_3$, $SiO_2$, SrO, and optionally $Y_2O_3$.

10. A therapeutic composition comprising a mixture of:
    (i) radioactive microparticles; and
    (ii) non-radioactive microparticles,
    wherein the non-radioactive microparticles have a radiopacity of greater than 6,000 Hounsfield Units (HU) at 120 kVp, and have a level of radioactivity that is less than 0.15 GBq/gram,
    wherein the radioactive microparticles comprise about 40 wt % $Y_2O_3$, about 20 wt % $Al_2O_3$, and about 40 wt % $SiO_2$, wherein at least a portion of the yttrium is yttrium-90,
    wherein the radioactive microparticles make up from about 10% to about 80% of the total mass of microparticles in the composition; and
    wherein the mixture of the radioactive microparticles and the non-radioactive microparticles has an overall specific activity that is 0.4 GBq/g or greater.

11. The composition according to claim 10, wherein the radioactive microparticles have an average density from about 1.0 $g/cm^3$ to about 4.5 $g/cm^3$; and the non-radioactive microparticles have an average density from 1.0 $g/cm^3$ to about 4.5 $g/cm^3$.

12. The composition according to claim 10, wherein the radioactive microparticles and the non-radioactive microparticles have a difference in particle densities that is within 30% of the average of the two particle densities.

13. The composition according to claim 10, wherein the radioactive microparticles have an average diameter from about 10 to about 1200 microns; and the non-radioactive microparticles have an average size from about 10 to about 1200 microns.

14. The composition according to claim 10, wherein the radioactive microparticles and the non-radioactive microparticles have a difference in average sizes that is within 40% of the average of the two averages sizes.

15. The composition according to claim 10, wherein the radioactive microparticles and the non-radioactive microparticles have a relative drag ratio from about 0.95:1 to about 1:0.95, wherein the relative drag ratio is calculated by dividing the fall time for the radioactive microparticles by the fall time for the non-radioactive microparticles.

16. The composition according to claim 10, wherein the radioactive microparticles make up about 25% of the total mass of microparticles in the composition.

17. The composition according to claim 10, wherein the radioactive microparticles and the non-radioactive microparticles have a specific gravity from about 3.3 to about 3.9 with reference to water, and have an average diameter from about 20 to about 40 microns.

18. The composition according to claim 10, wherein the non-radioactive microparticles comprise yttrium-89.

19. The composition according to claim 10, wherein the non-radioactive microparticles comprise $Ga_2O_3$, $SiO_2$, SrO, and optionally $Y_2O_3$.

20. The composition of claim 1, wherein the radioactive microparticles have a level of radioactivity that is at least 4.0 GBq/gram.

21. The composition of claim 10, wherein the radioactive microparticles have a level of radioactivity that is at least 4.0 GBq/gram.

22. A composition comprising a mixture of:

(i) radioactive microparticles; and (ii) non-radioactive microparticles, wherein the radioactive microparticles:

make up from about 10% to about 80% of the total mass of microparticles in the composition, and comprise about 40 wt % $Y_2O_3$, about 20 wt % $Al_2O_3$, and about 40 wt % $SiO_2$, wherein at least a portion of the yttrium is yttrium-90;

wherein the non-radioactive microparticles:

comprise about 40 wt % $Y_2O_3$, about 20 wt % $Al_2O_3$, and about 40 wt % $SiO_2$, and have a level of radioactivity that is less than 0.15 GBq/gram; and wherein the mixture of the radioactive microparticles and the non-radioactive microparticles has an overall specific activity that is 0.4 GBq/g or greater.

23. The composition according to claim 22, wherein the radioactive microparticles and the non-radioactive microparticles have sizes, surface areas, shapes, particle densities, and surface conditions that result in particles with a relative drag ratio of about 1.0.

24. The composition according to claim 23, wherein the radioactive microparticles and the non-radioactive microparticles have substantially the same: sizes, surface areas, shapes, particle densities, and surface conditions.

25. The composition according to claim 22, wherein the difference in particle densities of the radioactive and non-radioactive microparticles is within 30% of the average of the two particle densities.

26. The composition according to claim 22, wherein the difference in average sizes of the radioactive and non-radioactive microparticles is within 40% of the average of the two averages sizes.

27. The composition according to claim 22, wherein the radioactive microparticles are microparticles formed from neutron activation of particles identical to the non-radioactive microparticles.

28. The composition according to claim 22, wherein the radioactive microparticles and the non-radioactive microparticles have sizes, surface areas, shapes, and particle densities that result in a relative drag ratio from about 0.95:1 to about 1:0.95, wherein the relative drag ratio is calculated by dividing the fall time for the radioactive microparticles by the fall time for the non-radioactive microparticles; and wherein the radioactive microparticles and the non-radioactive microparticles are suitable for administration to a vascularized tumour.

29. The composition of claim 22, wherein the radioactive microparticles have a level of radioactivity that is at least 4.0 GBq/gram.

* * * * *